United States Patent

Suzuki

[11] Patent Number: 5,807,273
[45] Date of Patent: Sep. 15, 1998

[54] OPHTHALMIC APPARATUS

[75] Inventor: Nobuo Suzuki, Nukata-gun, Japan

[73] Assignee: Nidek Co., Ltd., Gamagori, Japan

[21] Appl. No.: 755,646

[22] Filed: Nov. 25, 1996

[30] Foreign Application Priority Data

Nov. 30, 1995 [JP] Japan ............................... 7-337909

[51] Int. Cl.⁶ .................................................. A61B 5/00
[52] U.S. Cl. .................................................. 600/558
[58] Field of Search .............................. 128/645, 745;
600/558; 351/208–210, 221

[56] References Cited

U.S. PATENT DOCUMENTS

| | | | |
|---|---|---|---|
| 4,682,595 | 7/1987 | Hoerenz et al. | 128/395 |
| 5,139,022 | 8/1992 | Lempert | 128/633 |
| 5,279,300 | 1/1994 | Miwa et al. | 128/648 |
| 5,406,076 | 4/1995 | Mimura et al. | 250/229 |

FOREIGN PATENT DOCUMENTS

A-8-66364  12/1996  Japan.

*Primary Examiner*—Max Hindenburg
*Attorney, Agent, or Firm*—Oliff & Berridge, PLC

[57] ABSTRACT

An ophthalmic apparatus comprising an observing optical system and performing alignment through the observing optical system to position a measuring system at a predetermined position in relation to an eye to be examined comprises a detecting system for detecting whether an eyelid of the eye is within a predetermined opening condition at the time of a completion of alignment, a judging system for judging whether the opening condition of the eyelid is sufficient for measurement based on detection results detected by the open eyelid detecting means, and an informing system for informing the opening condition of the eyelid based on judgement results judged by the open eyelid condition judging means.

18 Claims, 5 Drawing Sheets

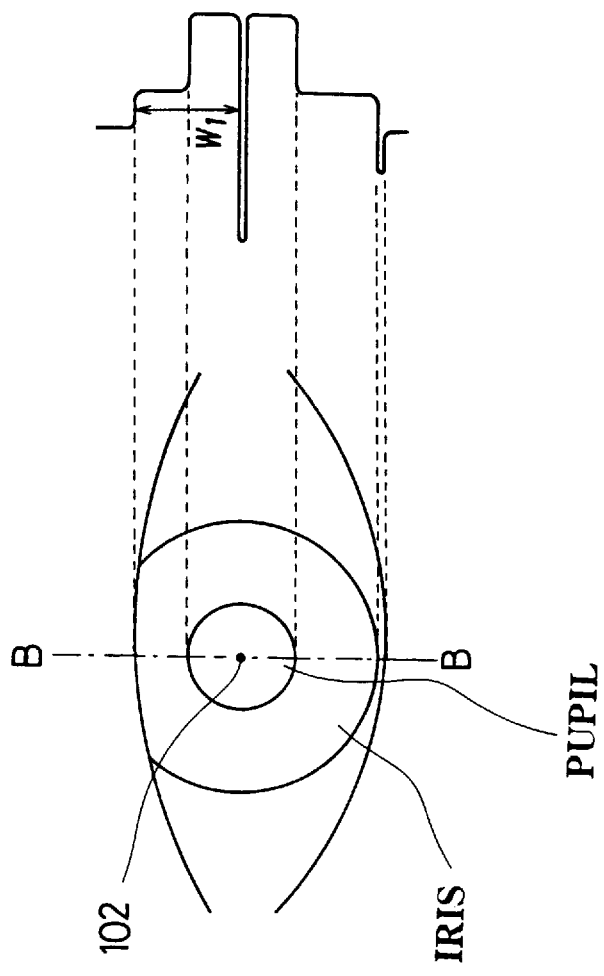

OPHTHALMIC APPARATUS

BACKGROUND OF THE INVENTION

1. Field of the Invention

The present invention relates to an ophthalmic apparatus for measuring optical characteristics of an eye to be examined, and more particularly to a mechanism to detect an opening condition of eyelids of the eye to be examine.

2. Description of Related Art

Conventionally, for ophthalmic apparatuses for examining and measuring optical characteristics of the eye of an examinee, there have been known a non-contact type tonometer and a corneal shape measurement apparatus and the like. In an apparatus of this type, measurement is performed by projecting air or luminous for measurement onto the eye to be examined. To obtain precise measurement data, it is important for the above apparatus to conduct measurement in the condition that the eye to be examined is widely opened so that the air and the luminous flux for measurement can be projected to the eye without being eclipsed by an eyelid of the eye.

In the conventional ophthalmic apparatus, generally, a determination of whether an opening condition of the eye (the eyelid) is sufficient for the measurement is made by an examiner. If it is not sufficient, the examiner instructs the examinee to open his eye more widely before measurement.

However, the judgement on an opening condition of the eye by the examiner while observing the eye is left to examiner's subjective judgement, thus the degree of precision of the judgement would depend on skills and the like of the examiner. Accordingly, some examiners perform measurement without noticing the opening condition being insufficient; therefore, it causes errors in measurement, or dispersion of measurement data even if measurement can be completed.

In particular, in the apparatus that measurement is automatically performed after the completion of alignment, there would be a case that measurement is started as soon as alignment is completed even if an opening condition of the eye to be examined is insufficient; accordingly, unnecessary measurements are carried out and precise measurement data can not be obtained. This would sometimes impose a load on the examiner and the examinee.

SUMMARY OF THE INVENTION

The present invention has been made in view of the above circumstances and has an object to overcome the above problems and to provide an ophthalmic apparatus capable of preventing unnecessary measurement on an eye to be examined as being opened insufficiently for measurement and of performing effective measurement whereby to obtain measurement data with high reliance.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, (1) an ophthalmic apparatus of this invention comprising an observing optical system and performing alignment through the observing optical system to position a measuring system at a predetermined position in relation to an eye to be examined, comprising means for detecting whether an eyelid of the eye is within a predetermined opening condition at the time of a completion of alignment, means for judging whether the opening condition of the eyelid is sufficient for measurement based on a signal representing a detection result detected by the open eyelid detecting means, and means for informing the opening condition of the eyelid based on a signal representing a judgement result judged by the open eyelid condition judging means.

(2) In the above ophthalmic apparatus (1), the open eyelid detecting means may comprise means for projecting index on a cornea of the eye outside of an area necessary for measurement, and an optical system for detecting an image representing the index produced on the cornea through the index projecting optical system.

(3) In the ophthalmic apparatus (2), the open eyelid index projecting means may comprise a light source for emitting near infrared light and an objective lens to project the light emitted by the light source onto the cornea of the eye thereby to form an index image on the same, and the open eyelid index detecting optical system comprises a field stop with an aperture having a predetermined diameter designed to allow the index in the completion of alignment state to pass therethrough and to restrict luminous flux irregularly reflected by the eyelid, and a light receiving element for receiving the light passing through the field stop.

(4) In the ophthalmic apparatus (1), the informing means may comprise a monitor display means or a sound producing means.

(5) In the ophthalmic apparatus (2), the open eyelid index projecting means may project a plurality of indexes on the cornea of the eye to be examined.

(6) In the ophthalmic apparatus (2), the open eyelid condition judging means may judges whether an index image is formed on the cornea or not on the basis of a light quantity detected by the open eyelid index detecting optical system.

(7) The ophthalmic apparatus (1) may further comprise a television camera to take a photograph of the anterior part of the eye in order to observe the eye to be examined, the television camera being used in common with the open eyelid detecting means.

(8) The ophthalmic apparatus (1) may further comprise a television camera to take a photograph of the anterior part of the eye in order to observe the eye to be examined, wherein the open eyelid detecting means detects an opening condition of the eye by applying a picture processing to an image taken with the television camera.

(9) In the second aspect of the present invention, an ophthalmic apparatus comprising an observing optical system and performing alignment through the observing optical system to position a measuring system at a predetermined position in relation to an eye to be examined, comprises means for detecting whether an eyelid of the eye is within a predetermined opening condition at the time of a completion of alignment, means for judging whether the opening condition of the eyelid is sufficient to measure based on a signal representing a detection result detected by the open eyelid detecting means, means for generating a trigger signal to activate the measuring system, and means for controlling the trigger signal generating means to be able to generate the trigger signal when the open eyelid condition judging means judges that the eye to be examined is opened sufficiently for measurement.

(10) In the ophthalmic apparatus (9), the open eyelid detecting means may comprise means for projecting index on a cornea of the eye outside of an area necessary for the measurement, and an optical system for detecting an image representing the index produced on the cornea through the index projecting optical system.

(11) In the ophthalmic apparatus (10), the open eyelid index projecting means may project a plurality of indexes on the cornea of the eye to be examined.

(12) In the ophthalmic apparatus (10), the open eyelid condition judging means may judges whether an index image is formed on the cornea or not on the basis of a light quantity detected by the open eyelid index detecting optical system.

(13) The ophthalmic apparatus (9) may further comprise means for projecting alignment index to the cornea, means for detecting an image representing the alignment index projected by the alignment index projecting means, means for judging whether an alignment state of the eye is proper or not based on a signal representing a result detected by the alignment index detecting means, wherein when the judging means judges that the alignment state is proper, a determination of whether the opening condition of the eyelid is sufficient for measurement is made by the open eyelid detecting means and the open eyelid condition judging means.

(14) In the ophthalmic apparatus (13), the alignment index projecting means may comprise a front index projecting optical means and a distance index projecting optical means, and the alignment index detecting means comprises a front index detecting optical means and a distance index detecting optical means.

(15) The ophthalmic apparatus (9) may further comprise input means for generating a trigger signal to activate the measuring system, wherein an input signal generated by the input means is not accepted when the open eyelid condition judging means judges that an opening condition of the eye is not sufficiently for measurement.

(16) In the ophthalmic apparatus (15), the input means may comprise switch means.

(17) The ophthalmic apparatus (9) may further comprise a television camera to take a photograph of the anterior part of the eye in order to observe the eye to be examined, the television camera being used in common with the open eyelid detecting means.

(18) The ophthalmic apparatus (9) may further comprise a television camera to take a photograph of the anterior part of the eye in order to observe the eye to be examined, wherein the open eyelid detecting means detects an opening condition of the eye by applying a picture processing to an image taken with the television camera.

According to the present invention, it is possible to prevent unnecessary measurement on the eye whose opening condition is insufficient, so that measurement data with high reliance can be obtained. In particular, in case that after the completion of alignment the apparatus generates a trigger signal to automatically start measurement, the measurement on the eye as the eyelid is opened insufficiently can be prevented from starting, making it possible to reduce the load imposed on both the examiner and examinee.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

FIG. 6 is an explanatory view of showing an example of detecting an opening condition of eyelids through a picture image processing procedure.

DETAILED DESCRIPTION OF THE PREFERRED EMBODIMENTS

A detailed description of one preferred embodiment of an ophthalmic apparatus embodying the present invention will now be given referring to the accompanying drawings. In the following embodiment, a non-contact type tonometer will be explained as an example of the ophthalmic apparatus.

Figure 1:
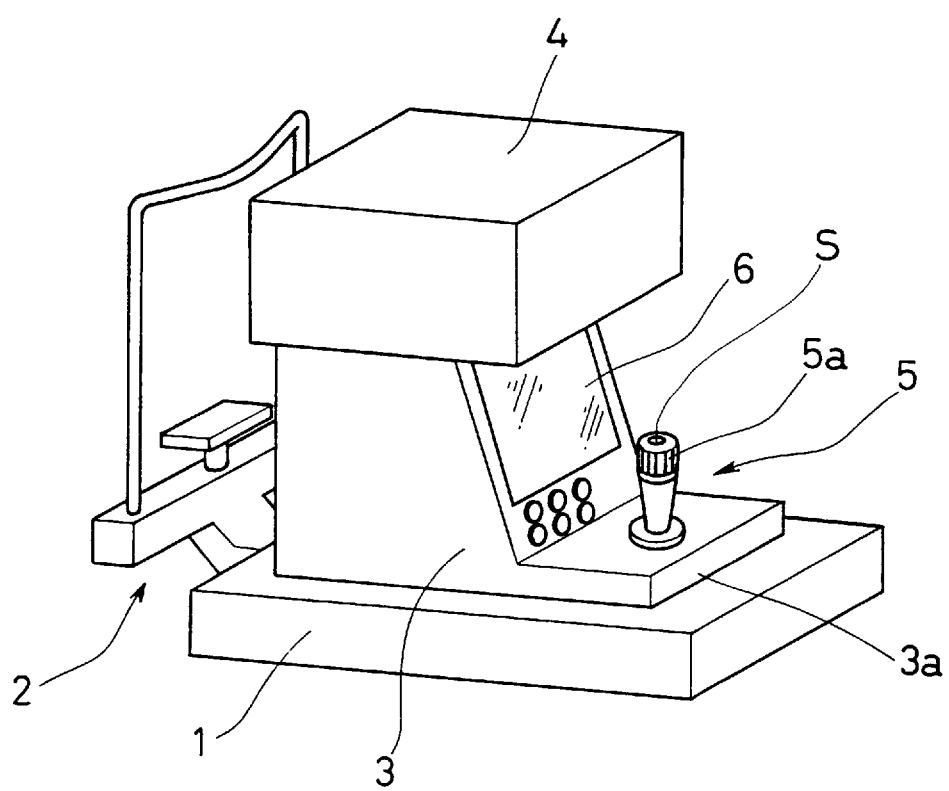
FIG. 1 is a perspective view of an outer appearance of a noncontact tonometer in the first embodiment.

FIG. 1 is an perspective view of an outer appearance simplified of a noncontact tonometer in the first embodiment.

A base 1 is provided with a chin rest 2 for supporting an eye to be examined at a predetermined position in relation to an apparatus. On the base 1, provided are a main body 3 and a measuring part 4 housing an optical system mentioned later therein. A joystick 5 is to move the main body 3 and the measuring part 4 respectively; in detail, by the operation of the joy stick 5, the main body 3 is moved forward and backward and to the right and left on the horizontal plane of the base 1 and the measuring part 4 is moved up and down with respect to the main body 3. In particular, concerning the movement of the main body 3 on the base 1, a fine movement of the main body in a horizontal direction can be realized by a construction of a spherical portion and a lower end portion provided at the lower side of a shaft of the joystick 5, a sliding plate whose lower end is capable of swinging, a friction plate attached on the base 1, and a bearing inside of a housing 3a formed integratedly with the main body 3.

The joystick 5 further comprises a rotating knob 5a provided at an upper periphery of the joystick 5, a slit plate which will rotate simultaneously with the rotation of the rotating knob 5a, and a light source and a light receiving element which are fixed in the shaft so as to be opposite to each other about the slit plate. With this joystick 5, the movement of the measuring part 4 upward and downward, i.e., vertically with respect to the main body 3 is made by detecting a rotating direction and a rotating amount of the rotating knob 5a based on a signal of the light receiving element, and a motor for moving the measuring part 4 up and down is activated based on the detection result. The detail mechanism of the above joystick 5 has been described in U.S. Pat. No. 5,406,076 assigned to the assignee of the present invention and its description is hereby incorporated by reference.

Reference number 6 is a television monitor to display the image of an anterior part of the eye and indication information to an examiner for alignment.

Figure 2:
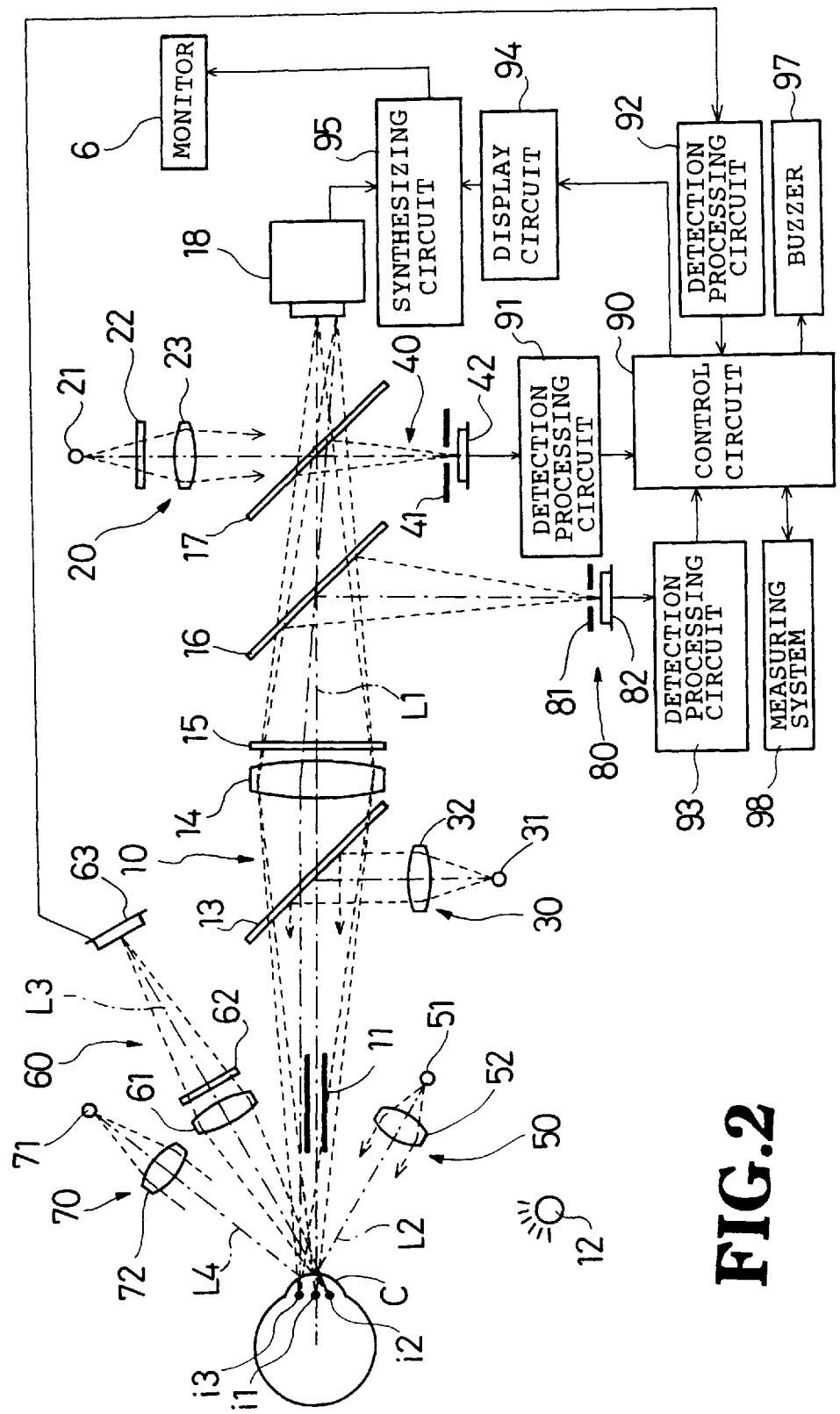
FIG. 2 is a schematic diagram of an optical system and a control system of the apparatus.

FIG. 2 shows a side view of the optical system and a plane view of a main construction of a control system of the apparatus in the embodiment.

A noncontact tonometer is an apparatus to measure intraocular pressure of an eye by projecting a compressed air onto a cornea of the eye to be examined thereby to deform it, detecting a deformation of the cornea into a predetermined state and directly or indirectly the air pressure when the cornea is deformed into the predetermined form.

This measuring mechanism itself has little relation to the present invention; therefore, the explanation described in U.S. Pat. No. 5,279,300 assigned to the assignee of the present invention, the title of which is Noncontact Type Tonometer, is hereby incorporated by reference.

Optical System

The optical system will be explained separately about an alignment optical system and an open eyelid index projecting and detecting optical system to detect an opening condition of an eyelid of the eye to be examined.

(Alignment optical system)

An observing optical system 10 has an optical axis denoted by L1. On the optical path of the observing optical system 10, arranged is a nozzle 11 for injecting air fluid to deform a cornea of an eye to be examined, an axis coincides with the optical axis L1 On the optical axis L1, coaxially arranged are a beam splitter 13, an objective lens 14, a filter 15, beam splitters 16 and 17, and a TV camera 18. Two light sources 12 (one of them is not shown in the figure) are to illuminate the anterior part of the eye to be examined from a lower side, which emits near-infrared light having a wavelength of 950 nm.

The filter 15 has the property of allowing the luminous flux having a wavelength of 950 nm emitted from the light sources 12 and other light sources of a front index projecting optical system 30 and an open eyelid index projecting optical system 70 both mentioned later to pass therethrough, and not allowing the luminous flux having a wavelength of 800 nm emitted from a light source of a distance index projecting optical system 50 to pass therethrough, making it possible to prevent unnecessary noise light from falling on the TV camera 18, a front index detecting optical system 40, and an open eyelid index detecting optical system 80, respectively.

A reticle projecting optical system 20 comprises a light source 21 for projecting a reticle, a reticle plate 22 on which a circular mark is formed, and a projection lens 23. When the reticle plate 22 is illuminated by the light source 21, the light representing the reticle passes through the projection lens 23, and is reflected by the beam splitter 17 toward the TV camera 18. The light of the reticle produces an image of a circular reticle on an image plane of the TV camera 18 and is superposed over the image of the anterior part of the eye.

A front index projecting optical system 30 is constructed of a light source 31 for projecting a front index and a projection lens 32. The light source 31 emits near-infrared light having a wavelength of 950 nm equal to that of the light source 12. The output frequency of the luminous flux emitted by the light source 31 is modulated to have a predetermined frequency in order to prevent the luminous flux emitted by the illumination light source 12 and the open eyelid index projecting optical system 70 from becoming noise light to a front index detecting optical system 40. This makes it possible to distinguish the luminous flux emitted by the light source 31 from the luminous flux emitted by each of the light sources 12 and 70.

The light emitted by the light source 31 is collimated by the projection lens 32. The collimated light is reflected by the beam splitter 13 so as to travel along the optical axis L1 and irradiate the cornea C of the eye to be examined. The luminous flux is then specularly reflected by the cornea C and forms an index i1 which is a virtual image of the light source 31. The luminous flux of the index i1 is directed back through the observing optical system 10, falls on the TV camera 18, and forms an index image on the imaging plane of the TV camera 18.

A front index detecting optical system 40 comprises a field stop 41, a two dimensional position detecting element 42. The field stop 41 has an aperture having a diameter designed so as to prevent unnecessary light from falling on the detecting element 42. For the two dimensional position detecting element 42, various sensors such as a charge coupled device (CCD), a position sensor detector (PSD) or the like can be used selectively.

After specularly reflected by the cornea C, the luminous flux representing the front index travels through the beam splitter 13, the objective lens 14, the filter 15, and the beam splitter 16 in turn, and is reflected by the beam splitter 17 toward the front index detecting optical system 40. The luminous flux then passes through the field stop 41 and falls on the light receiving element 42. This light receiving element 42 detects the position of the eye E in a vertical direction and in a right and left direction with respect to the measuring optical axis (an observing optical axis L) based on the two-dimensional position of the luminous flux of the index i1 fallen on an image plane of the detecting element 42.

A distance index projecting optical system 50 comprises a light source 51 for projecting a distance index and an objective lens 52 arranged on an optical axis L2. The light source 51 emits light having a wavelength of 800 nm different from that of the light source 31. The optical axis L2 is designed so as to incline with respect to the optical axis L1 of the observing optical system 10 and also to intersect the same at a predetermined working distance from the nozzle 11.

The light emitted by the light source 51 is collimated by the projection lens 52, and travels along the optical axis L2 onto the cornea C. The luminous flux specularly reflected by the cornea C to form an index i2 which is a virtual image of the light source 51.

A distance index detecting optical system 60 has an optical axis L3. The optical axis L3 and the optical axis L2 are symmetrical with respect to the optical axis L1, and the optical axis L3 intersects the optical axis L2 on the optical axis L1.

On the optical axis L3, coaxially arranged are a light receiving lens 61, a filter 62, and a one-dimensional position detecting element 63. The filter 62 has the property of allowing the light having a wavelength of 800 nm emitted by the light source 51 to pass therethrough and not allowing the light having a wavelength of 950 nm emitted by the illumination light source 12 and others to pass therethrough, thereby to prevent noise light from falling on the one-dimensional detecting element 63.

The luminous flux emitted by the light source 51 and reflected by the cornea, representing the index i2 is focused by the light receiving lens 61 and through the filter 62 onto the one-dimensional position detecting element 63. When the eye moves along the optical axis L1, namely, in a forward and backward direction, the image of the index i2 is simultaneously moved on an image plane of the one-dimensional detecting element 63 in its detection direction. Accordingly, the position of the eye is detected base on the basis of the displacement amount of the index image formed on the one-dimensional detecting element 63 from a correct position.

In FIG. 2, for convenience of explanation, the distance index projecting optical system 50 and the distance index detecting optical system 60 are arranged at an upper and a lower sides with respect to the eye to be examined, whereas preferably both optical systems are arranged in a horizontal direction.

(Open eyelid index projecting and detecting optical system)

An open eyelid index projecting optical system 70 comprises an optical axis L4 and is arranged so that a corneal reflection luminescent spot is formed just below the eyelid of the eye to be examined. On the optical axis L 4, provided are a light source 71, such as a LED and the like which emits infrared light having a wavelength of 950 nm, and a projection lens 72. The light emitted by the light source 71 is collimated by the projection lens 72, and travels along the optical axis L4 to the cornea C to irradiate it. The luminous flux specularly reflected by the cornea C forms an index i3, i.e., a virtual image of the light source 71 just below the eyelid when the eyelid of the eye in a predetermined alignment state is opened more widely than a predetermined allowable range.

An open eyelid index detecting optical system 80 is constructed of a field stop 81 and a light receiving element 82. The luminous flux of the index i3 passes through the beam splitter 13, the objective lens 14, and the filter 15, and is reflected by the beam splitter 16 toward the detecting optical system 80. The field stop 81 is arranged at a position substantially conjugated with the index i3 through the objective lens 14. The field stop 81 has an aperture at a position where the luminous flux of the index i3 will pass through. The diameter of the aperture is designed so as to allow only the luminous flux of the index i3 to pass therethrough after the completion of alignment and to restrict the passing of the luminous flux irregularly reflected by the eyelid, the detail will be mentioned later. An opening condition of the eyelid is detected on the basis of the quantity of light falling on the image plane of the light receiving element 82.

Control system

The system in the apparatus is constructed of a control circuit 90, a front index detection processing circuit 91, a distance index detection processing circuit 92, an open eyelid index detection processing circuit 93, a display circuit 94, a synthesizing circuit 95, an alarming buzzer 97, and a measuring system 98. The display circuit 94 produces characters such as messages to be informed to the examiner and marks for alignment. A character signal of the display circuit 94 is inputted to the synthesizing circuit 95. This synthesizing circuit 95 synthesizes the character signal inputted and a picture image signal provided from the TV camera 18 to output a synthesized signal to the monitor 6.

Operation of the above constructed apparatus will be explained.

Figure 3:
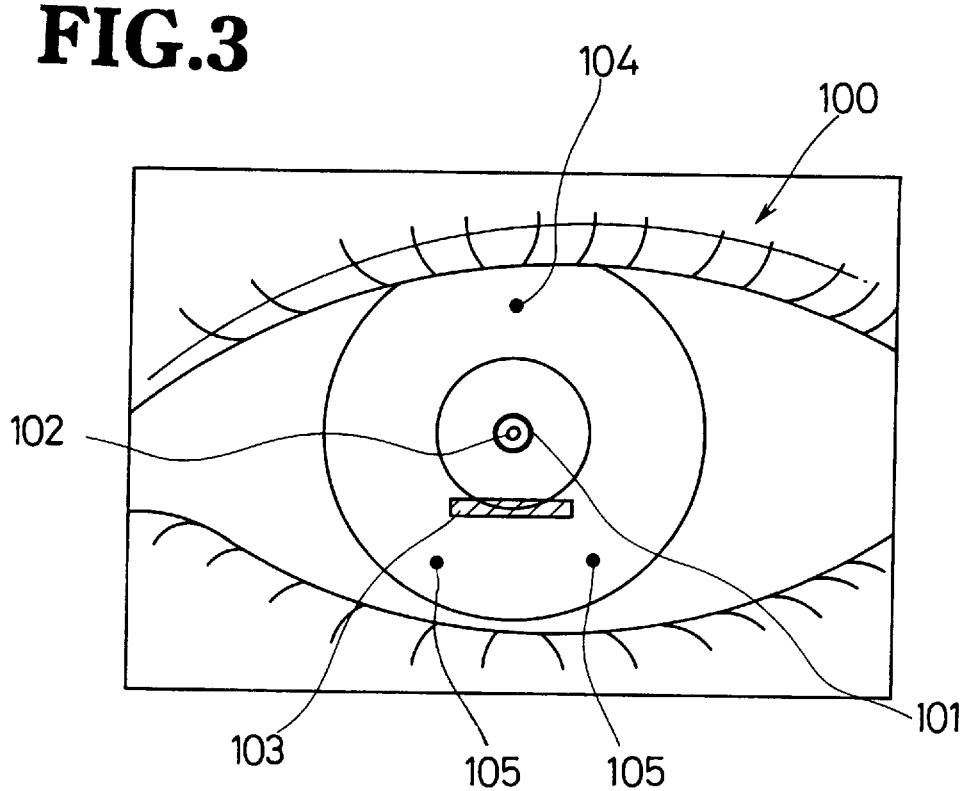
FIG. 3 is a pictorial view as an display example of a picture image displayed on a monitor of the apparatus in the embodiment.

At first, the alignment operation of the apparatus will be described. When the anterior part of the eye is illuminated by the illumination light source 12, the picture thereof is received through the observing optical system 10 by the TV camera 18. At this time a reticle image formed by the reticle optical system 20 is also received by the TV camera1 18. The picture image signal received by the TV camera 18 is transmitted through the synthesizing circuit 95 to the monitor 6 to display thereon. FIG. 3 shows an example of the picture displayed on the monitor 6. In FIG. 3, displayed are an image 100 of the anterior part of the eye, a reticle image 101, a front index image 102, a distance mark 103, an index image 104 produced through the open eyelid index projecting optical system, and images 105 produced by the illumination light sources 12 illuminating the anterior part of the eye.

While observing the anterior part image 100 and the reticle image 101 displayed on the monitor 6, the examiner operates the joystick 5 so that the reticle image 101 is positioned near the center of the iris or pupil of the eye to adjust the focus of the apparatus, making roughly alignment. In this state, the luminous flux representing the index i1 falls on the two-dimensional position detecting element 42 and the image plane of the TV camera 18 respectively, so that the front index image 102 is displayed on the monitor 6. When the luminous flux of the index i2 falls on the one-dimensional detecting element 61, the distance mark 103 will be displayed on the monitor 6.

The distance mark 103 is displayed as follows. The control circuit 90 processes a detection signal transmitted from the one-dimensional detecting element 63 by a predetermined process to obtain the distance between the nozzle 11 and the cornea C of the eye to be examined. Based on the data relating the distance transmitted from the control circuit 90, the display circuit 94 generates a character signal representing the distance mark 103 and a position signal representative of the position of the distance mark 103 on the monitor 6. The synthesizing circuit 95 synthesizes the picture signal provided from the TV camera 18 and the signal representative of the distance mark 103 to output the synthesized signals on the monitor 6. According to the actual distance between the nozzle 11 and the cornea C, the distance mark 103 moves in real-time above and below relative to the reticle image 101 on the monitor 6. It is superposed on the reticle image 101 when the cornea is positioned at a proper working distance with respect to the apparatus.

The examiner also operates the joystick 5 while observing the monitor 6 to move the apparatus so that the front index image 102 enters in the circular reticle image 101, making alignment in a vertical and lateral directions. Alignment in the working distance direction is, as mentioned above, performed by moving the apparatus with the joystick 5 so that the distance mark 103 is superposed on the reticle image 101. At this time, simultaneously with the alignment operation by the examiner, the control circuit 90 judges the completion of alignment by detecting whether the images representing the indexes i1 and i2 produced on the two-dimensional position detecting element 42 and the one-dimensional position detecting element 63 respectively enter within an allowable area or not.

After the completion of alignment, the control circuit 90 judges an opening condition of the eyelid of the eye to be examined as described below.

Figure 4A:
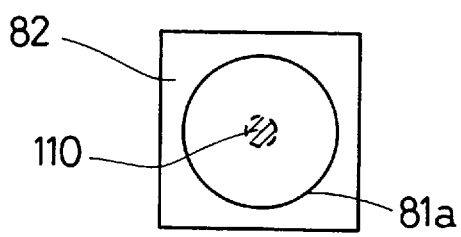
FIGS. 4 (a) and (b) are pictorial views of showing conditions of luminous flux being incident onto a light receiving element of an open eyelid index detecting optical system.

When the eyelid is opened more widely than a measurable area, the luminous flux of the index i3 produced by the light specularly reflected by the cornea C passes through the aperture 81a of the field stop 81 of the open eyelid index detecting optical system 80 and then falls on the image plane of the light receiving element 82. FIG. 4 (a) shows a state of the incident luminous flux at this time, in which reference number 110 is the distribution of the light incident on the light receiving element 82. As shown in the figure, the luminous flux representing the index i3 can almost pass through the aperture 81a of the field stop 81, thus falling on the image plane of the light receiving element 82.

Figure 4B:
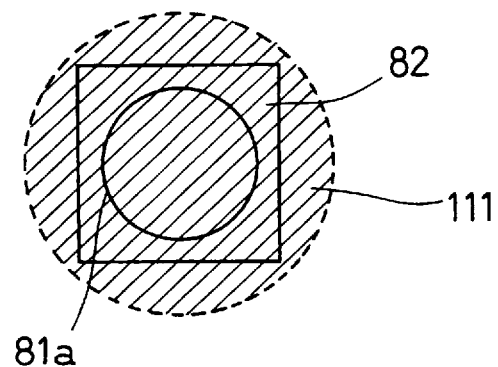

On the other hand, when the eyelid is not opened widely, the luminous flux emitted by the light source 71 of the open eyelid index projecting optical system 70 does not form an index image, and irregularly reflected by the surface of the eyelid and scattered. The scattered light travels along the same path as the light reflected by the cornea and falls on the open eyelid index detecting optical system 80. FIG. 4(b)

shows a state of the scattered light falling on the image plane of the light receiving element 82, in which the distribution of the scattered light is wider than the aperture 81a, so that only a part of the luminous flux restricted by the aperture 81a falling on the light receiving element 82.

The control circuit 90 judges an opening condition of the eyelid on the basis of the output of the light receiving element 82. In particular, when the eyelid is sufficiently opened, almost the light representing the index i3 passing through the aperture 81a of the field stop 81 comes to fall on the image plane of the light receiving element 82, increasing the output level therefrom. To the contrary, when the eyelid is not sufficiently opened, only a part of the scattered light restricted by the aperture 81a of the field stop 81 falls on the image plane, so that the output level from the light receiving element 82 is lower than the luminous flux of the index i3 as mentioned above. Accordingly, setting in advance a threshold value to judge an opening condition of the eyelid based on the output level makes it possible to detect the above two conditions of the eyelid.

When judged that the eyelid is opened sufficiently for measurement as above, the control circuit 90 transmits automatically a trigger signal to start a measurement to measuring system 98 to activate the same. Consequently, it obtains measurement data.

When judged that the eyelid is not sufficiently opened because the eyelid covers the measurement allowable area on the cornea, the control circuit 90 does not generate the trigger signal, whereas drives the display circuit 94 and the synthesizing circuit 95 to display a message on the monitor 6 to request the examinee to open his eye more sufficiently. At the same time, the control circuit 90 drives the buzzer 97 to make a sound to demand to open the eye to be examined widely.

The examiner therefore instructs the examinee to open his eye. Here, when an alignment state becomes off, the examiner makes again an alignment operation while observing the displayed images on the monitor 6. After the completion of the alignment, similarly, if judges based on the output signal of the light receiving element 82 that the eye to be examined is sufficiently opened, the control circuit 90 transmits a trigger signal to start a measurement.

As mentioned above, the apparatus performs measurement after judging an opening condition of the eyelid of the eye to be examined, making it possible to prevent measurement on the eye with the eyelid opened insufficiently. As a result, it is possible to obtain measurement data with high reliance and less error.

In the above mentioned embodiment, the apparatus detects an alignment state and automatically transmits a trigger signal to perform measurement, whereas the trigger signal may be generated with a switch S (see FIG. 1) manually operated by the examiner. In this case of the trigger signal inputted with the switch S by the examiner, the trigger signal can not be accepted when it is judged that the opening condition of the eyelid is insufficient and an instruction to more widely open the eye to be examined is informed by a message displayed on the monitor and a sound of the buzzer.

Figure 5:
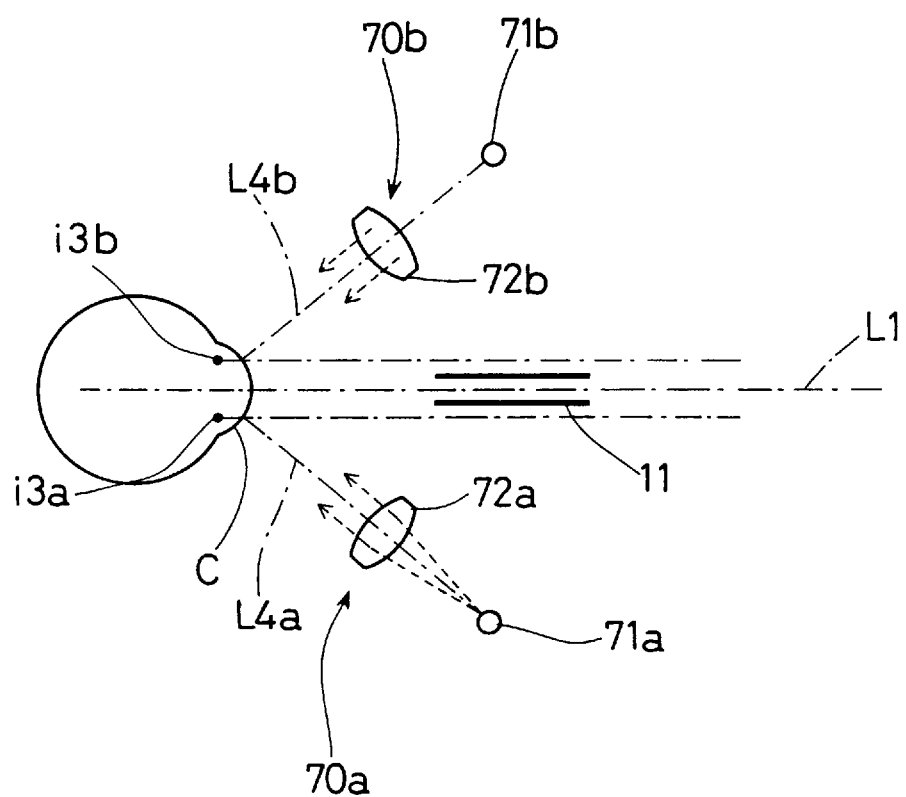
FIG. 5 is a schematic diagram in a modified embodiment of the open eyelid index projecting optical system.

In the above embodiment, the number of the index projected by the open eyelid index projecting optical system 70 is one, whereas it may be plural. For example, in case of providing two sets of the open eyelid index projecting optical system 70, as shown in FIG. 5 which shows two optical systems 70a and 70b viewed from above, the optical systems 70a and 70b are arranged so that the optical axes L4a and L4b thereof are directed from symmetrically and obliquely side above to the cornea C to produce images representing index i3a and i3b, i.e., virtual images of the light sources of the optical systems 70a and 70b respectively. The above arrangement makes it possible to irradiate the eye to be examined from side thereof; therefore, it becomes easy to project index light even to an examinee with sharply-chiseled feature.

In this case, to correspond with two index images i3a and i3b, the open eyelid index detecting optical system 80 is provided with two apertures on the field stop 81 and two light receiving elements 82. Judgement on an opening condition of the eyelid is made based on whether the two light receiving elements both have detected corresponding index images or either one has detected an index image. This judgement may properly be determined in consideration of a distinction between right and left eyes, a measurable area, and others.

It is further possible to judge an opening condition of the eye based on a picture image taken with the TV camera 18 without providing an open eyelid index detecting optical system. In detail, at the completion of alignment, the luminous flux of the index i3 produced by the open eyelid index projecting optical system 70 also falls on the image plane of the TV camera 18; accordingly, an area to detect the image of the index i3 is determined on the image plane as similar to that of the field stop 80. The light quantity within the area on the image plane is detected and compared, as well as the case of the light receiving element 82, with the standard threshold value set in advance, thus the judgement on whether an opening condition of the eyelid is sufficient to measure the eye is made.

Furthermore, without providing an open eyelid index projecting optical system, it is possible to detect an opening condition of the eyelid by applying a picture image signal processing procedure to the anterior part image of the eye taken with the TV camera 18. For example, a memory of the apparatus takes a picture image of the anterior part of the eye at the completion of alignment therein and processes the picture image by a picture image processing to find the boundary edges of pupil, iris, and eyelid based on a difference in luminance therebetween within an area necessary for measurement. As shown in FIG. 6, for instance, the opening condition of the eyelid is detected based on whether the width W1 of the iris detected on the basis of the index image 102 from a signal representative of the light quantity in a B—B line in the figure is wider than the area needed for measurement.

It is also possible to use the front index detecting optical system and the open eyelid index detecting optical system in common if a position detecting element such as a CCD and the like is used therefor. The position detecting element is constructed so that at the completion of alignment both images representing a front index and an open eyelid index fall on the position detecting element. At this time, both index images are distinguished by the application of modulation to one of the light sources of the index projecting optical systems. Judgement on an opening condition of the eyelid is made based on a signal representing the light quantity within the area in advance determined on the positional detecting element as well as the above mentioned method.

The present invention may be embodied in other specific forms without departing from the spirit or essential characteristics thereof. For instance, the illumination light source for illuminating the anterior part of the eye to be examined and the light source for projecting an open eyelid index may be used in common. It is possible to detect an opening condition of the eyelid even during measurement, and stop the measurement if an error occur and display the occurrence of the error in a message.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising an observing optical system and performing alignment through the observing optical system to position a measuring system at a predetermined position in relation to an eye to be examined, comprising:

means for detecting whether an eyelid of the eye is within a predetermined opening condition at the time of a completion of alignment;

means for judging whether the opening condition of the eyelid is sufficient for measurement based on a signal representing a detection result detected by said open eyelid detecting means; and means for informing the opening condition of the eyelid based on a signal representing a judgement result judged by said open eyelid condition judging means.

2. An ophthalmic apparatus according to claim 1, wherein said open eyelid detecting means comprises means for projecting index on a cornea of the eye outside of an area necessary for measurement, and an optical system for detecting an image representing the index produced on the cornea through said index projecting optical system.

3. An ophthalmic apparatus according to claim 2, wherein said open eyelid index projecting means comprises a light source for emitting near infrared light and an objective lens to project the light emitted by the light source onto the cornea of the eye thereby to form an index image on the same, and said open eyelid index detecting optical system comprises a field stop with an aperture having a predetermined diameter designed to allow the index in the completion of alignment state to pass therethrough and to restrict luminous flux irregularly reflected by the eyelid, and a light receiving element for receiving the light passing through the field stop.

4. An ophthalmic apparatus according claim 1, wherein said informing means comprises a monitor display means or a sound producing means.

5. An ophthalmic apparatus according to claim 2, wherein said open eyelid index projecting means projects a plurality of indexes on the cornea of the eye to be examined.

6. An ophthalmic apparatus according to claim 2, wherein said open eyelid condition judging means judges whether an index image is formed on the cornea or not on the basis of a light quantity detected by said open eyelid index detecting optical system.

7. An ophthalmic apparatus according to claim 1, further comprising a television camera to take a photograph of the anterior part of the eye in order to observe the eye to be examined, said television camera being used in common with said open eyelid detecting means.

8. An ophthalmic apparatus according to claim 1, further comprising a television camera to take a photograph of the anterior part of the eye in order to observe the eye to be examined, wherein said open eyelid detecting means detects an opening condition of the eye by applying a picture processing to an image taken with the television camera.

9. An ophthalmic apparatus comprising an observing optical system and performing alignment through the observing optical system to position a measuring system at a predetermined position in relation to an eye to be examined, comprising:

means for detecting whether an eyelid of the eye is within a predetermined opening condition at the time of a completion of alignment;

means for judging whether the opening condition of the eyelid is sufficient to measure based on a signal representing a detection result detected by said open eyelid detecting means;

means for generating a trigger signal to activate said measuring system; and means for controlling said trigger signal generating means to be able to generate the trigger signal when said open eyelid condition judging means judges that the eye to be examined is opened sufficiently for measurement.

10. An ophthalmic apparatus according to claim 9, wherein said open eyelid detecting means comprises means for projecting index on a cornea of the eye outside of an area necessary for the measurement, and an optical system for detecting an image representing the index produced on the cornea through said index projecting optical system.

11. An ophthalmic apparatus according to claim 10, wherein said open eyelid index projecting means projects a plurality of indexes on the cornea of the eye to be examined.

12. An ophthalmic apparatus according to claim 10, wherein said open eyelid condition judging means judges whether an index image is formed on the cornea or not on the basis of a light quantity detected by said open eyelid index detecting optical system.

13. An ophthalmic apparatus according to claim 9, further comprising, means for projecting alignment index to the cornea;

means for detecting an image representing said alignment index projected by said alignment index projecting means;

means for judging whether an alignment state of the eye is proper or not based on a signal representing a result detected by said alignment index detecting means;

wherein when said judging means judges that the alignment state is proper, a determination of whether said opening condition of the eyelid is sufficient for measurement is made by said open eyelid detecting means and said open eyelid condition judging means.

14. An ophthalmic apparatus according to claim 13, wherein said alignment index projecting means comprises a front index projecting optical means and a distance index projecting optical means, and said alignment index detecting means comprises a front index detecting optical means and a distance index detecting optical means.

15. An ophthalmic apparatus according to claim 9, further comprising input means for generating a trigger signal to activate said measuring system, wherein an input signal generated by said input means is not accepted when said open eyelid condition judging means judges that an opening condition of the eye is not sufficiently for measurement.

16. An ophthalmic apparatus according to claim 15, wherein said input means comprises switch means.

17. An ophthalmic apparatus according to claim 9, further comprising a television camera to take a photograph of the anterior part of the eye in order to observe the eye to be examined, said television camera being used in common with said open eyelid detecting means.

18. An ophthalmic apparatus according to claim 9, further comprising a television camera to take a photograph of the anterior part of the eye in order to observe the eye to be examined, wherein said open eyelid detecting means detects an opening condition of the eye by applying a picture processing to an image taken with the television camera.

* * * * *